United States Patent
Vlach et al.

(10) Patent No.: US 10,034,617 B2
(45) Date of Patent: *Jul. 31, 2018

(54) SYSTEM AND METHOD FOR ELECTRO-CARDIOGRAM (ECG) MEDICAL DATA COLLECTION WHEREIN PHYSIOLOGICAL DATA COLLECTED AND STORED MAY BE UPLOADED TO A REMOTE SERVICE CENTER

(71) Applicant: Braemar Manufacturing, LLC, Eagan, MN (US)

(72) Inventors: Erich Vlach, San Diego, CA (US); Charles Gropper, Mission Viejo, CA (US)

(73) Assignee: BRAEMAR MANUFACTURING, LLC, Eagan, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/339,442

(22) Filed: Oct. 31, 2016

(65) Prior Publication Data

US 2017/0042442 A1  Feb. 16, 2017

Related U.S. Application Data

(63) Continuation of application No. 14/688,891, filed on Apr. 16, 2015, which is a continuation of application (Continued)

(51) Int. Cl.
*G06F 13/38* (2006.01)
*A61B 5/0432* (2006.01)
(Continued)

(52) U.S. Cl.
CPC ........ *A61B 5/04325* (2013.01); *A61B 5/0006* (2013.01); *A61B 5/0408* (2013.01);
(Continued)

(58) Field of Classification Search
CPC .............. A61B 5/04286; A61B 5/0006; G06F 13/4068
See application file for complete search history.

(56) References Cited

U.S. PATENT DOCUMENTS

| 3,934,267 A | 1/1976 | Kosaka et al. |
| 5,462,051 A | 10/1995 | Oka et al. |

(Continued)

FOREIGN PATENT DOCUMENTS

| EP | 1559366 A1 | 8/2005 |
| EP | 2000085 A2 | 12/2008 |

(Continued)

OTHER PUBLICATIONS

European Search Report for EP11838752.1, dated Aug. 21, 2015.
(Continued)

*Primary Examiner* — Tammara Peyton

(57) ABSTRACT

A data collection unit obtains physiological data from a subject interface on a subject. The subject interface can be connected to the data collection unit. When the subject interface is connected to the data collection unit, subject interface contacts on the subject interface make contact with data collection unit contacts on the data collection unit. Some of the data collection unit contacts are for communicating physiological data from the subject interface to the data collection unit. Some of the contacts are for powering the data collection unit upon the subject interface being connected to the data collection unit and for powering down the data collection unit upon the subject interface being disconnected from the data collection unit.

20 Claims, 13 Drawing Sheets

Related U.S. Application Data

No. 13/287,968, filed on Nov. 2, 2011, now Pat. No. 9,021,161.

(60) Provisional application No. 61/409,521, filed on Nov. 2, 2010.

(51) Int. Cl.
*G06F 13/40* (2006.01)
*A61B 5/0428* (2006.01)
*G06F 3/06* (2006.01)
*A61B 5/00* (2006.01)
*A61B 5/0408* (2006.01)
*G06F 19/00* (2018.01)

(52) U.S. Cl.
CPC ........ *A61B 5/04286* (2013.01); *G06F 3/0619* (2013.01); *G06F 3/0655* (2013.01); *G06F 3/0679* (2013.01); *G06F 13/4068* (2013.01); *G06F 19/3406* (2013.01); *G06F 19/3481* (2013.01); *A61B 2560/045* (2013.01); *G06F 19/323* (2013.01); *G06F 2206/1014* (2013.01)

(56) References Cited

U.S. PATENT DOCUMENTS

| | | | |
|---|---|---|---|
| 5,678,562 A | 10/1997 | Sellers | |
| 6,117,077 A | 9/2000 | Del Mar et al. | |
| 6,223,080 B1 | 4/2001 | Thompson | |
| 6,564,090 B2 | 5/2003 | Taha et al. | |
| 6,597,943 B2 | 7/2003 | Taha et al. | |
| 6,976,958 B2 | 12/2005 | Quy | |
| 7,361,188 B2 | 4/2008 | Barr | |
| 7,598,878 B2 | 10/2009 | Goldreich | |
| 7,615,007 B2 | 11/2009 | Shults et al. | |
| 7,794,406 B2 | 9/2010 | Reisfeld et al. | |
| 8,082,027 B2 | 12/2011 | Young et al. | |
| 8,144,948 B2 | 3/2012 | Krachman | |
| 8,185,623 B2 * | 5/2012 | Lewis | G06F 19/322 340/539.12 |
| 8,370,549 B2 | 2/2013 | Burton et al. | |
| 8,787,119 B2 * | 7/2014 | Sorias | G04C 10/00 368/204 |
| 8,790,259 B2 | 7/2014 | Katra et al. | |
| 8,909,832 B2 | 12/2014 | Vlach et al. | |
| 9,021,161 B2 | 4/2015 | Vlach et al. | |
| 9,028,404 B2 * | 5/2015 | DeRemer | A61B 5/0002 600/300 |
| 2002/0165458 A1 | 11/2002 | Carter et al. | |
| 2003/0028442 A1 | 2/2003 | Wagstaff et al. | |
| 2004/0229478 A1 | 11/2004 | Chen | |
| 2005/0251003 A1 | 11/2005 | Istvan et al. | |
| 2005/0251055 A1 | 11/2005 | Zhirnov et al. | |
| 2006/0100530 A1 | 5/2006 | Kliot et al. | |
| 2006/0149594 A1 | 7/2006 | Hilligoss et al. | |
| 2007/0142738 A1 * | 6/2007 | Hung | A61B 5/02438 600/519 |
| 2007/0167694 A1 * | 7/2007 | Causevic | A61B 5/0402 600/301 |
| 2007/0197878 A1 | 8/2007 | Shklarski | |
| 2007/0265541 A1 * | 11/2007 | Hung | A61B 5/0006 600/523 |
| 2008/0218799 A1 | 9/2008 | Hiew et al. | |
| 2008/0234592 A1 | 9/2008 | Lim et al. | |
| 2008/0243020 A1 | 10/2008 | Chou | |
| 2009/0018456 A1 | 1/2009 | Hung | |
| 2009/0049213 A1 * | 2/2009 | Chen | G06F 13/385 710/104 |
| 2009/0171227 A1 | 7/2009 | Dziubinski et al. | |
| 2009/0326612 A1 | 12/2009 | Distler | |
| 2010/0004522 A1 | 1/2010 | Varela | |
| 2010/0063407 A1 | 3/2010 | Huang | |
| 2010/0099954 A1 | 4/2010 | Dickinson et al. | |
| 2010/0268103 A1 | 10/2010 | McNamara et al. | |
| 2011/0009729 A1 * | 1/2011 | Shin | A61B 5/04286 600/391 |
| 2011/0112413 A1 | 5/2011 | Panescu et al. | |
| 2011/0160553 A1 | 6/2011 | Talbot et al. | |
| 2011/0237924 A1 | 9/2011 | McGusty et al. | |
| 2012/0029299 A1 * | 2/2012 | DeRemer | A61B 5/0002 600/300 |
| 2012/0108934 A1 | 5/2012 | Valdes et al. | |
| 2012/0110226 A1 | 5/2012 | Vlach et al. | |
| 2012/0110228 A1 | 5/2012 | Vlach et al. | |
| 2013/0225938 A1 | 8/2013 | Vlach | |
| 2016/0135696 A1 | 5/2016 | Cobbett et al. | |

FOREIGN PATENT DOCUMENTS

| | | |
|---|---|---|
| EP | 2030565 A1 | 3/2009 |
| EP | 2383859 A1 | 11/2011 |
| JP | 4089030 B2 | 3/1992 |
| JP | H06 197875 A | 7/1994 |
| JP | 2004147994 A | 5/2004 |
| WO | WO-2009041127 A1 | 4/2009 |
| WO | WO-2010103164 A1 | 9/2010 |

OTHER PUBLICATIONS

European Search Report for EP11838752.1, dated Dec. 14, 2015.
European Search Report for EP11838757.0, dated Aug. 4, 2015.
International Search Report for PCT/US2011/058976, dated Mar. 7, 2012.
International Search Report for PCT/US2011/058998, dated Mar. 12, 2012.

* cited by examiner

SYSTEM AND METHOD FOR ELECTRO-CARDIOGRAM (ECG) MEDICAL DATA COLLECTION WHEREIN PHYSIOLOGICAL DATA COLLECTED AND STORED MAY BE UPLOADED TO A REMOTE SERVICE CENTER

CROSS REFERENCE TO RELATED APPLICATIONS

This application is a continuation of U.S. patent application Ser. No. 14/688,891, filed Apr. 16, 2015, which is a continuation of U.S. patent application Ser. No. 13/287,968 know U.S. Pat. No. 9,021,161), filed Nov. 2, 2011, which claims priority to U.S. Provisional Application Ser. No. 61/409,521, entitled "Medical Data Collection Apparatus", filed on Nov. 2, 2010, the entire contents of which are incorporated herein by reference.

BACKGROUND

Physiological activity of various organs, such as the heart or brain, can be monitored, and this physiological activity can be analyzed to look for patterns that may assist in diagnosing various conditions. For example, the electrical activity of the heart can be monitored to track various aspects of the functioning of the heart. Cardiac electrical activity can be indicative of disease states or other physiological conditions ranging from benign to fatal. Cardiac monitoring devices can sense the cardiac electrical activity of a living being.

SUMMARY

This document describes systems and techniques by which physiological data for an individual (e.g., a patient or test subject) can be obtained corresponding to a physiological characteristic such as cardiac activity and analysis of that physiological activity can be performed by a remote data processing center. For example, a subject can be provided with a physiological data collection device such as a monitoring device for monitoring a physiological signal for events (e.g. arrhythmia events, QRS data, etc.), a recording device, or the like. The physiological data collection device can obtain, for example, ECG data from the subject for a predefined period of time and can store the ECG data on a storage medium in the physiological data collection device. As described in more detail below, the physiological data collection device can include a data connector such as a USB connector so the subject can directly connect the physiological data collection device to a computer system such as the subject's personal computer. Also, the physiological data collection device can be provided with program code that allows the subject to automatically upload the obtained physiological data to a remote data processing center when the physiological data collection device is connected to a computer using the USB connector.

The uploaded data can be analyzed by a computer running an analysis program at the remote data processing center. A medical professional, such as a doctor or a technician, can provide feedback regarding the analysis. Based on the analysis and the feedback, a report can be provided to the subject from the data processing center indicating the extent to which abnormal and/or clinically significant events were detected during the predefined period of time. The report can also include a recommendation to consult further with a physician based on clinically significant events identified in the uploaded data.

The physiological data collection device can include a subject interface and a data collection unit. The subject interface can physically interface with the subject for obtaining physiological data from the subject. The subject interface can include, for example, a lead-wire set having multiple electrode leads that are removably connected to the data collection unit. Data can be obtained using electrodes attached to the electrode leads and stored on non-volatile memory in the data collection unit. The data collection unit and/or the lead-wire set can be configured so that when the lead-wire set is connected to the physiological data collection unit, a data connector on the data collection unit is prevented from being connected to an external device such as the subject's personal computer.

Also, data can be automatically obtained from the subject interface by the physiological data collection device upon the subject interface being physically connected to the physiological data collection unit. Also, the physiological data collection device can also include a power supply that powers the physiological data collection device. The data collection unit and the subject interface can be configured such that the power supply powers the physiological data collection device only when the subject interface is connected to the physiological data collection unit. In some examples, the power supply can be included in the subject interface. When the power supply (e.g. a battery) dies, the subject interface, including the power supply, can be disposed of and a new subject interface with a fresh battery can be connected to the data collection unit so that the data collection unit can be re-used.

In a first aspect, a physiological data collection device can include an electro-cardiogram (ECG) lead-wire set; a data collection unit including: a data connector for connecting to an external computing device, a lead-wire set connector for connecting to the ECG lead-wire set, and non-volatile memory coupled with the data connector and the lead-wire set connector, and a processor programmed to obtain ECG data from the ECG lead-wire set and store the obtained ECG data in the non-volatile memory; and wherein the ECG lead-wire set or the data collection unit or both have one or more structural components that prevent a connection between the data connector and the computer when the ECG lead-wire set is connected to the data collection unit and vice versa.

Implementations can include any or all of the following features. The data connector can include a male USB connector. The lead-wire set includes a female receptacle that is configured to receive the male USB connector when the lead-wire set is connected to the data collection unit. The lead-wire set includes an electrode connector having lead-wire set contacts; the lead-wire set interface includes an electrode connector receptacle having data collection unit contacts; and the electrode connector receptacle is configured to receive the electrode connector such that the lead-wire set contacts make contact with the data collection unit contacts when the lead-wire set is connected to the data collection unit. The USB connector is configured to rotate into a recess in the data collection unit; and when the USB connector is rotated into the recess, the lead-wire set interface is exposed so that the lead-wire set can be connected to the data collection unit via the lead-wire set interface and the recess blocks a connection of the USB connector to the computer. The male USB connector includes standard USB contacts and customized data collection unit contacts; and the lead-wire set connects to the male USB connector such that the lead-wire set interface interfaces with the lead-wire set via the customized data collection unit contacts in the USB connector.

In another aspect, an electro-cardiogram (ECG) self-assessment kit includes: an ECG subject interface including one or more electrode leads; multiple ECG electrodes configured to connect to the one or more electrode leads; a power source; a portable subject ECG data collection unit including: a USB connector configured to interface with a USB port on a computer, non-volatile memory coupled with the USB connector, and a processor powered by the power source and programmed to obtain ECG data from the electrode leads and to store the ECG data in the non-volatile memory; and a medium storing program code that when run by the computer supports access to a remote data processing center for uploading the ECG data from the non-volatile memory to the remote data processing center when the USB connector is connected to a computer connected to a network.

Implementations can include any or all of the following features. The data collection unit includes the medium storing program code. The program code when run by the computer supports access to the remote data processing center for uploading the ECG data without installing a software application on the computer. The program code when run by the computer supports access to the remote data processing center by automatically initiating an application for uploading of the ECG data upon determining that the USB connector is connected to the computer. The program code including a link to a website where the ECG data can be uploaded. The program code supports access to the data processing center by supporting a download from a remote server system to the computer of a user application for uploading the ECG data to the remote data processing center. The subject interface is configured to be physically attached to the ECG data collection unit; and when the subject interface is connected to the ECG data collection unit, the USB connector is blocked so that the USB connector cannot be connected to the computer. The USB connector includes male USB connector that is received into a receptacle in the subject interface when the subject interface is connected to the data collection unit.

The non-volatile memory has sufficient memory to store ECG data for a predefined time period; and wherein the power source has sufficient power to power the data collection unit for the predefined time period. The program code, when run by the computer, obtains and presents an ECG assessment report from the data processing center. The subject interface includes: a clip for securing the subject interface to the data collection unit; and a lanyard that allows the data collection unit to be hung from the neck of a subject when the subject interface is secured to the data collection unit. The subject interface includes the power source.

In another aspect, a method of providing a data analysis service includes: providing a physiological data collection device to a subject, the physiological data collection device including: an electro-cardiogram (ECG) subject interface; a data collection unit including a USB data connector for connecting to a computer, an interface for connecting to the subject interface, non-volatile memory coupled with the data connector, and a processor programmed to obtain ECG data from the subject interface and store the ECG data in the non-volatile memory; obtaining, at a remote data processing center, the ECG data from the data collection unit when the data collection unit is connected to a USB data port on a computer having a network connection; analyzing the ECG data for arrhythmia events; obtaining a physician review of the ECG data; and providing a report over the network to the subject based on the analyzing the ECG data and based on the physician review.

Implementations can include any or all of the following features. The obtaining the ECG data includes obtaining the ECG data via a transmission of the ECG data over the network wherein the transmission initiates automatically upon a determining that the data collection unit is connected to the USB data port. The USB data connector includes a male USB data connector. Obtaining, at the remote data processing center, a unique identifier from the data collection unit; verifying based on the unique identifier that the physiological data collection device has been preauthorized for the steps of analyzing, obtaining a physician review, and providing; and performing the steps of analyzing, obtaining a physician review, and providing only upon successful verification. The verifying further includes determining that a data analysis service has not already been performed for the physiological data collection device.

The method further includes providing a medium storing program code that when run by the computer supports access to the remote data processing center for uploading the ECG data from the non-volatile memory to the remote data processing center when the USB data connector is connected to a computer connected to a network. The non-volatile memory includes the medium.

In another aspect, a subject electro-cardiogram (ECG) data collection device includes: a removable ECG subject interface having subject interface contacts; a power source; a data collection unit including: a processor programmed to obtain physiological data from the ECG subject interface and store the physiological data in non-volatile memory, a data connector configured to be physically connected to a universal data port on a computer, and data collection unit contacts configured to be physically connected to the subject interface contacts on the ECG subject interface; the physiological data collection device configured to provide power from the power source to the processor upon the ECG subject interface being connected to the data collection unit and to interrupt power from the power source upon disconnection of the ECG subject interface from the data collection unit.

Implementations can include any or all of the following features. The subject interface includes a lead-wire set. The ECG subject interface includes the power source. The data collection unit includes the non-volatile memory. The data connector includes a male USB connector. The physiological data collection device is further configured to detect power provided by the computer when the data connector is connected to the computer and to upload the physiological data stored in the non-volatile memory to a remote service center via the computer when the data connector is connected to the computer. The data collection unit is configured to stop providing power from the power source when the ECG subject interface is disconnected from the data collection unit. The subject interface contacts comprise a first subject interface contact and a second subject interface contact that: when not connected to a corresponding first data collection unit contact and a second data collection unit contact, are configured to create an open circuit, and when connected to the corresponding first data collection unit contact and a second data collection unit contact, are configured to create a closed circuit. The data collection unit is further configured to automatically obtain data from the ECG subject interface upon the ECG subject interface being connected to the data collection unit. The data collection unit is further configured to automatically stop obtaining data from the ECG subject interface upon the ECG subject interface being disconnected from the data collection unit. The first data collection unit contact is in series with the second data collection unit contact; and wherein the ECG subject interface, when connected to the data collection unit, is configured to bring the first data collection unit contact into electrical connection with the second data collection unit contact. The subject interface contacts include a third subject interface contact and a fourth subject interface contact for bringing electrodes on the ECG subject interface into electrical communication with the processor. The subject interface connector includes a fifth subject interface contact that is configured to interrupt the processor when the ECG subject interface is disconnected from data collection unit.

In another aspect, a method includes: powering an electro-cardiogram (ECG) data collection unit upon an ECG subject interface being physically connected to the ECG data collection unit, the connected ECG subject interface creating a closed circuit with a power source for powering the ECG data collection unit; obtaining, using a processor, data from the ECG subject interface and storing the data on non-volatile memory; and powering-off the ECG data collection unit upon the ECG subject interface being physically disconnected from the ECG data collection unit and thereby creating an open circuit with the power source.

Implementations can include any or all of the following features. The ECG subject interface includes a lead-wire set. The obtaining and the storing include obtaining and storing the data on non-volatile memory automatically upon the ECG subject interface being physically connected to the ECG data collection unit. The method further includes automatically initiating an upload, over a network, of the data stored on the non-volatile memory to a remote service center via a computer upon a data connector on the data collection unit being physically connected to the computer. The data connector includes a male USB connector; and wherein connecting the data connector on the ECG data collection unit with the computer includes connecting the USB connector with the computer. The ECG data collection unit includes a first data collection unit contact and a second data collection unit contact; wherein being physically connected includes bringing the first data collection unit contact into electrical communication with the second data collection unit contact via the ECG subject interface and thereby closing the circuit with the power source. The data collection unit includes a third data collection unit contact and a fourth data collection unit contact; and wherein being physically connected includes bringing a first and second electrodes on the ECG subject interface into electrical communication with the processor via the third data collection unit contact and the fourth data collection unit contact. The data collection unit includes a fifth data collection unit contact that contacts a fifth subject interface contact on the ECG subject interface when the ECG subject interface is connected to the data collection unit; and the method further includes sending an interrupt signal to the processor when the ECG subject interface is disconnected from the ECG data collection unit. The ECG subject interface includes the power source.

Details of one or more implementations are set forth in the accompanying drawings and the description below. Other features, aspects, and potential advantages will be apparent from the description and drawings, and from the claims.

DESCRIPTION OF DRAWINGS

Like reference symbols in the various drawings indicate like elements.

DETAILED DESCRIPTION

Figure 1:
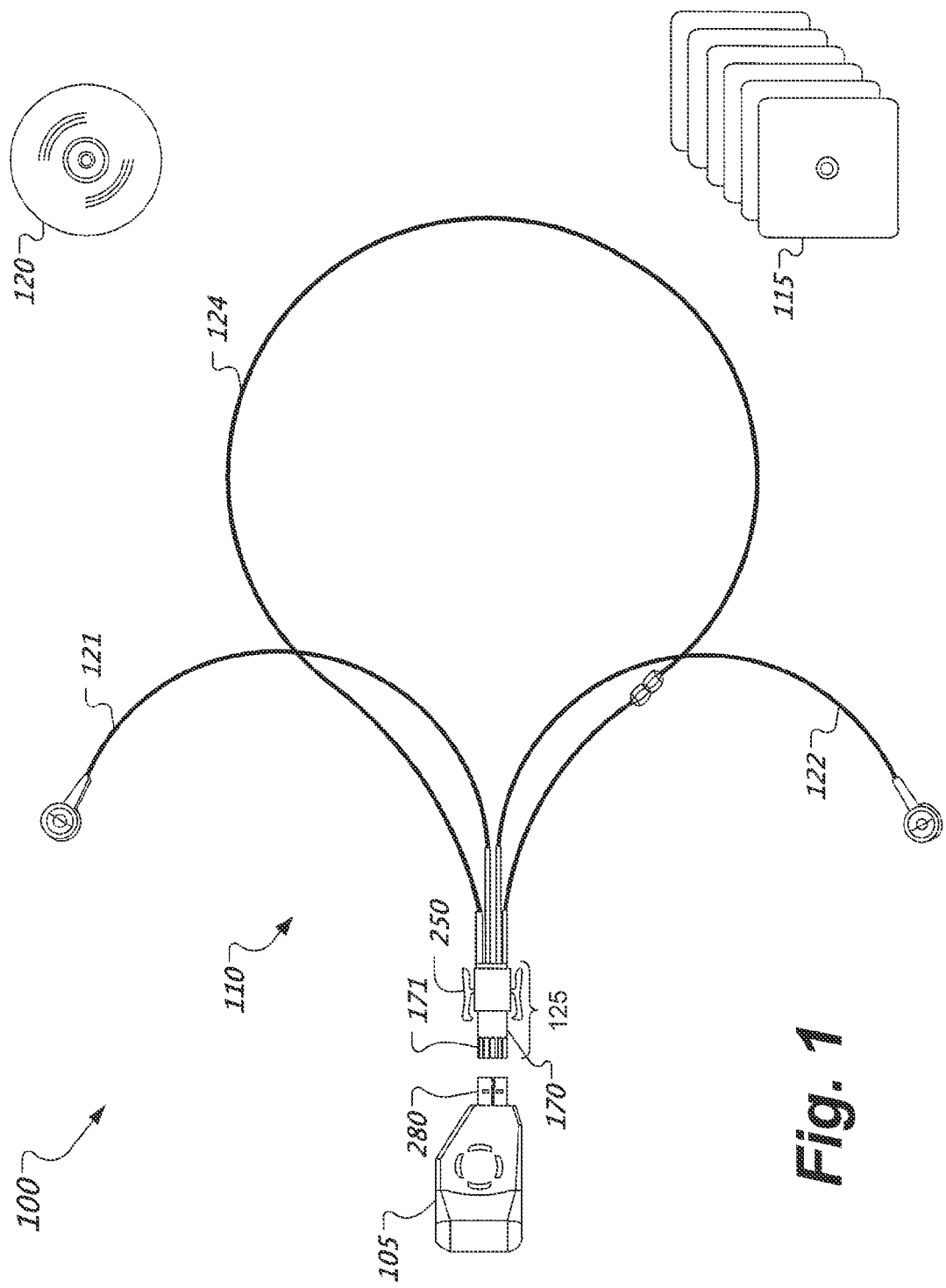
FIGS. 1-4 show various aspects of an example self-assessment kit for obtaining ECG data from a subject.

FIG. 1 shows an example of a self-assessment kit 100 for obtaining ECG data from a subject. The self-assessment kit 100 includes a data collection unit 105, a lead-wire set 110, electrodes 115 in the form of removable electrode patches, and program code 120 stored on a medium such as a CD-ROM. The self-assessment kit allows a subject to obtain his or her own ECG signal, upload ECG data to a remote data processing center, and obtain an assessment from the data processing center without the need to involve a third-party medical practitioner such as a prescribing physician. Also, the self-assessment kit can be configured to allow a subject to self-monitor his or her own ECG signal for a specified period of time such as 14 days.

The lead-wire set 110 has a connector head 125, a first electrode lead 121, and a second electrode lead 122. The connector head 125 is configured to be connected to the data collection unit 105. When connected, the data collection unit 105 can be hung from the neck of the subject using a lanyard 124 on the lead-wire set 110. The connector head 125 also includes an electrode connector 170. The electrode connector 170 is a male end with multiple lead-wire set contacts 171 at a distal end of the electrode connector 170.

The electrodes 115 are disposable electrode patches that can be connected to distal ends of the first electrode lead 121 and the second electrode lead 122. The electrodes 115 have adhesive backing so that they can be stuck to the chest of the subject. The self-assessment kit 110 can include enough disposable electrodes 115 for the specified period of time.

In use, the data collection unit 105 is connected to the connector head 125, and one of the electrode patches is connected to the first electrode lead 121 and another of the electrode patches is connected to the second electrode lead 122. A subject sticks the connected electrodes to his or her chest and wears the data collection unit 105 around his or her neck with the lanyard 124. The data collection unit 105 obtains an electrical signal from the electrode patches connected to the first electrode lead 121 and the second electrode lead 122. The electrical signal is converted to a digital signal and stored in the data collection unit 105 as ECG data.

Figure 2:
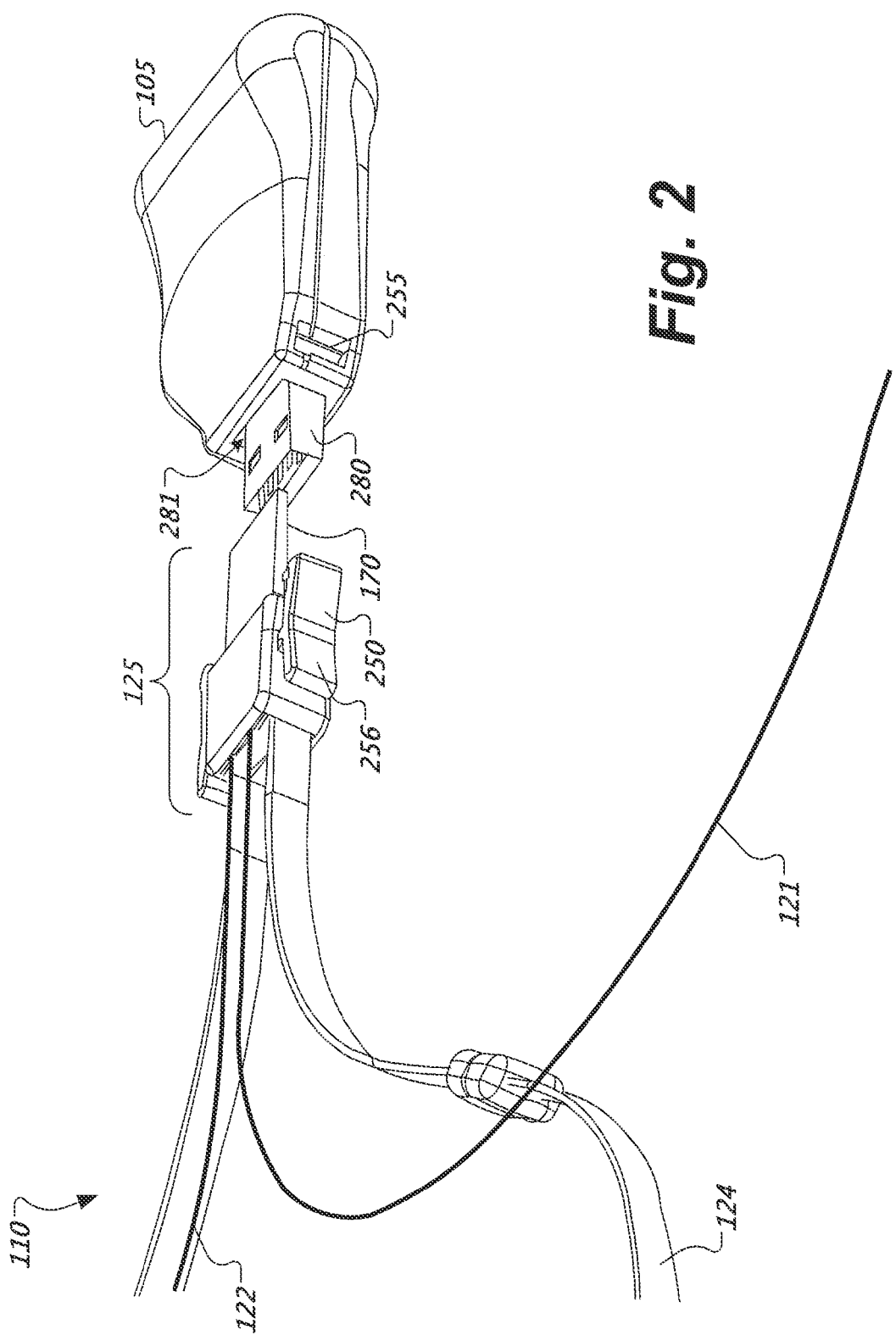

FIG. 2 shows a side perspective view of the data collection unit 105 and the lead-wire set 110. When the connector head 125 is connected to the data collection unit 105, a clip 250 on a side of the connector head 125 clips into a clip receptacle 255 on the data collection unit 105 to securely fasten the lead-wire set 110 to the data collection unit 105. The other side of the connector head 125 has a similar such clip. To remove the connector head 125 from the data collection unit 205, a user can depress a thumb tab 256 on the clip 250 to disengage the clip 250 from the clip receptacle 255.

Figure 3:
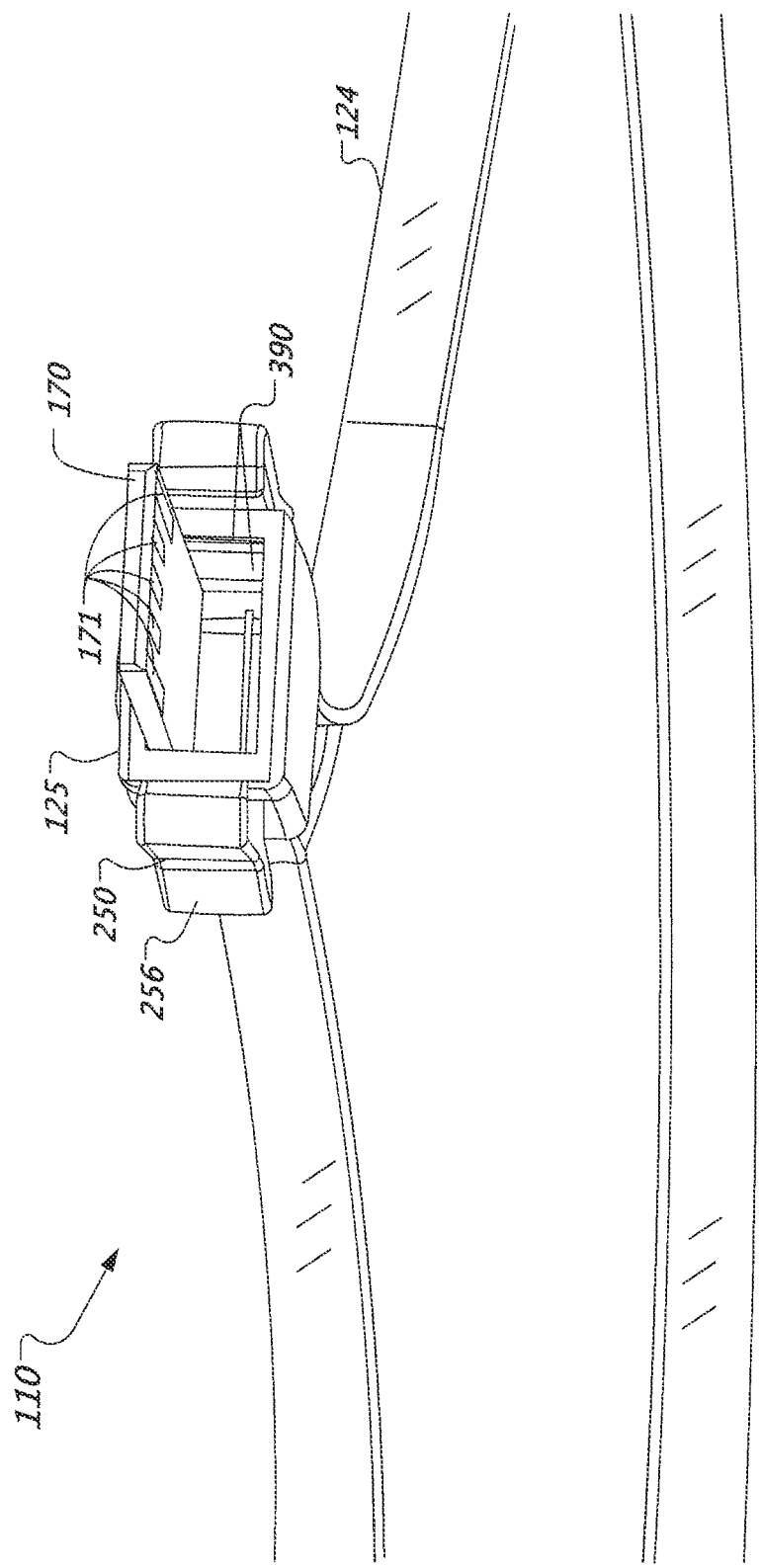
Figure 4:
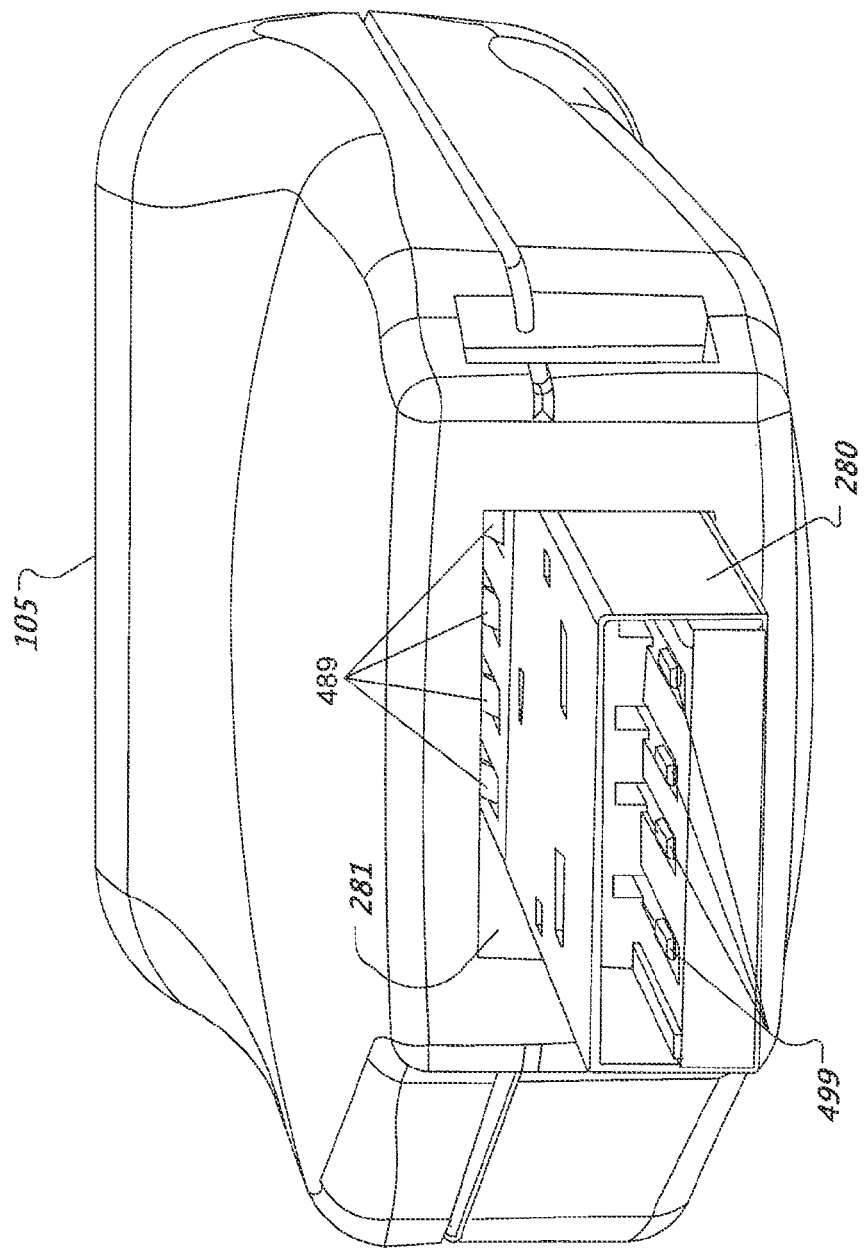

FIG. 3 shows a front perspective view of a portion of the lead-wire set 110, including the connector head 125. The connector head 125 has a USB connector receptacle 390 adjacent to the electrode connector 170. FIG. 4 shows a front perspective view of the data collection unit 105. The data collection unit 105 includes a male USB connector 280 and a female electrode connector receptacle 281 adjacent to the USB connector 280. The data collection unit 105 has data collection unit contacts 489 inside the electrode connector receptacle 281. The USB connector 280 also has standard USB contacts 499 inside the USB connector 280.

When the lead-wire set 110 is connected to the data collection unit 105, the electrode connector 170 on the connector head 175 is received into electrode connector receptacle 281 on the data collection unit 105, and the lead-wire set contacts 171 make contact with the data collection unit contacts 489. Also, when the connector head 125 is connected to the data collection unit 105, the USB connector 280 is received into the USB connector receptacle 390 on the connector head 125. In this manner, when the lead-wire set 110 is connected to the data collection unit 105, the USB connector 280 cannot simultaneously be connected to an external device such as a personal computer. This helps to protect a subject from simultaneously being connected with a power source for the data collection unit 105 and with another power source in an external device. Accordingly, there is no need to provide the data collection unit 105 with galvanic isolation circuitry to isolate the subject from the power source of an external device connected to the data collection unit 105 while the subject is connected to the data collection unit 105.

Also, when the lead-wire set 110 is connected to the data collection unit 105, data can automatically be obtained from the lead-wire set 110 and stored on the data collection unit 105. When the lead-wire set 110 is disconnected from the data collection unit 105, the data obtaining and storing can be terminated automatically.

Figure 5:
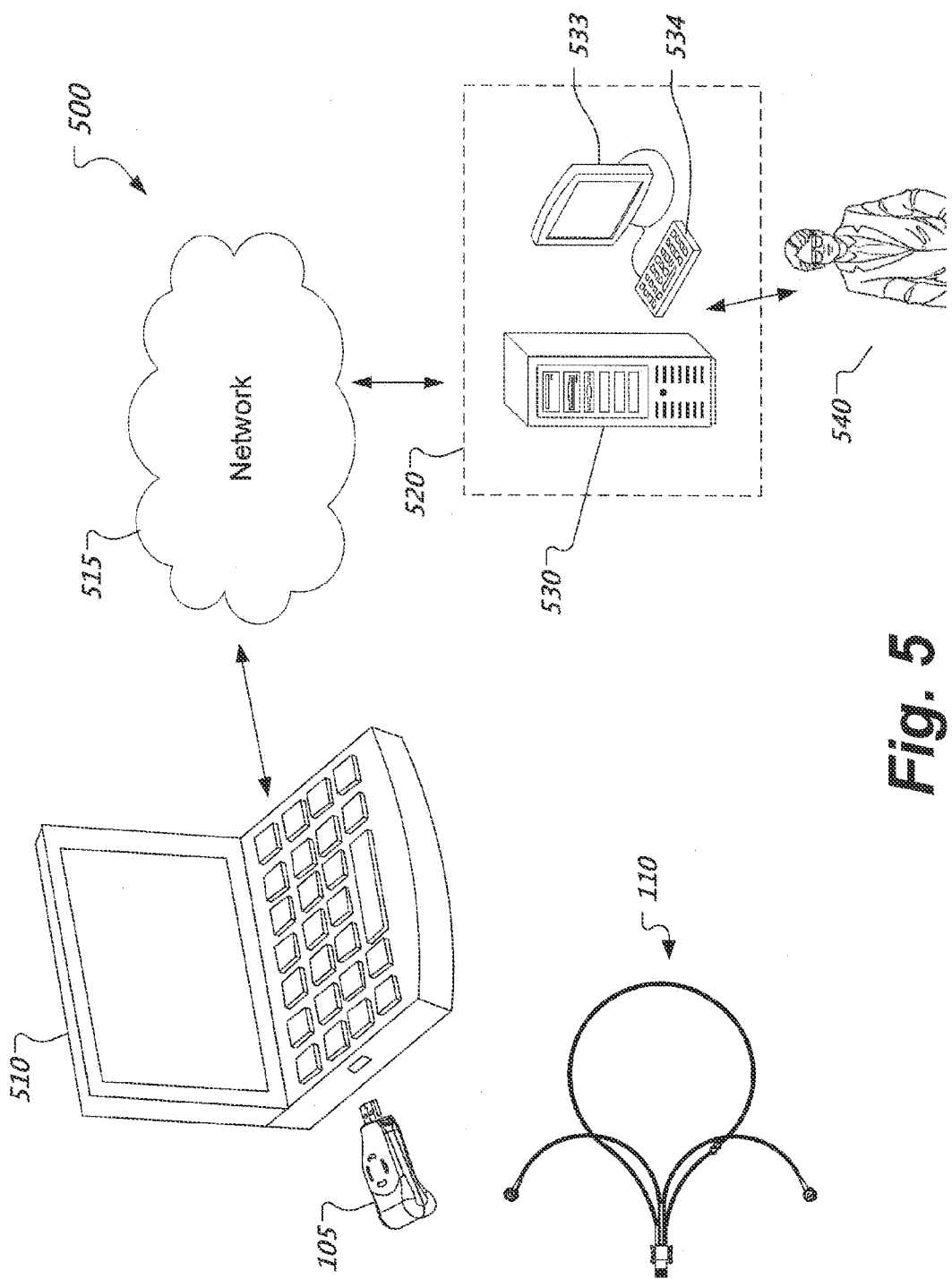
FIG. 5 shows an example system for uploading physiological data stored on a data collection unit.

FIG. 5 shows an example system 500 for uploading the ECG data stored on the data collection unit 105. The program code 120 can be run on a computer system 510 such as the subject's personal computer. The computer system 510 includes a computer and a display device. When the subject has completed the data collection period, the subject can disconnect the data collection unit 105 from the lead-wire set 110 and connect the USB connector 280 to the computer system 510. The program code when run by the computer system 510, supports access to a remote data processing center 520 so that the ECG data can be uploaded from the data collection unit 105 over a network 515 to the remote data processing center 520 where the physiological data is analyzed. The program code can support access to the remote data processing center 520 by automatically initiating a transmission of the ECG data stored on the data collection unit 105 upon detecting that the data collection unit 105 is connected to the computer system 510.

In some examples, the data processing center can obtain demographic data about the subject. Demographic data can assist in the analysis of the physiological data obtained from the data collection unit. For example, a particular event detected in a physiological signal can be serious for one person and not serious for another based on demographics such as age. The program code, when run by the computer system 510, can also facilitate the data processing center obtaining demographic data about the subject.

The data processing center 520 includes a computer 530 that analyzes the physiological data for abnormal and/or clinically significant events. The computer 530 can determine, using predefined algorithms, arrhythmias in the subject's ECG data and can provide a report to a medical professional 540, such as a medical technician and/or a doctor. The medical professional can review the reported arrhythmias in the subject's ECG signal from a display device 533 connected the computer 530 and provide feedback via input device 534 to the computer 530 as to which events were accurately identified and which events were inaccurately identified.

A report of the reviewed arrhythmic events can be compiled at the data processing center 520 and provided to the subject. The report can be provided to the subject over the network 515. The program code 120 can include code for a user application that presents the report to the subject from the subject's computer system 510.

The program code 120 can be stored on a medium such as CD ROM as shown in FIG. 1. In some examples, the program code can be stored on a medium on the data collection unit 105 such as non-volatile memory. In such an example, when the subject plugs the data collection unit 105 into the subject's computer system 510, the program code can be run by the subject's computer system 510 to support access to the remote data processing center 520 by automating the process of uploading the ECG from the data collection unit 105 to the data processing center 520, or by directing the subject to download, from a remote server system, an application for uploading the subject's ECG data. The program code stored on the data collection unit 105 can also include program code that runs when the subject plugs the data collection unit 105 into the subject's computer system 510 and directs the subject to an external location such as a website for uploading the ECG data on the data collection unit 105 without installing an application on the subject's computer system 510.

A subject can use the self-assessment kit 100 to self-monitor by plugging the lead-wire set 110 into the data collection unit 105 which in turn powers the data collection unit 105 and lead-wire set 110 and initiates recording of data from the lead-wire set 110 to memory on the data collection unit 105. When the subject is ready to upload the data to the remote data processing center, the subject can unplug the lead-wire set from the data collection unit 105 which powers down the data collection unit 110 and lead-wire set and stops recording of data. The subject can then plug the data collection unit 105 into the computer 510 connected to the network 515. The data can be automatically uploaded to the remote data processing center 520.

In some examples, the computer 510 can include a public terminal such as a kiosk specifically provided for obtaining the subject data from the data collection unit and uploading the subject data to the data processing center 520. The public terminal is provided in a public location such as in a health care facility like a doctor's office, a pharmacy, or the like. The public terminal can be pre-loaded with a program for obtaining the data from the data processing device and uploading the data over the network 515 to the data processing center 520. The public terminal can also be configured to obtain the demographic information from the subject when the subject uploads the data. A report from the data processing center 520 can be viewed or printed directly from the public terminal.

In some examples, the subject can provide the data collection unit 110 to a third-party for uploading the data to the data processing center 520. For example, the self-assessment kit can include a pre-paid package for mailing the data collection unit 110 to a third-party or directly to the data processing center. The kit 100 can also include a questionnaire for the subject to fill-out to provide demographic data to facilitated analysis by the data processing center 520 and to provide a location for a report to be sent to the subject either by mail or electronically.

Figure 6:
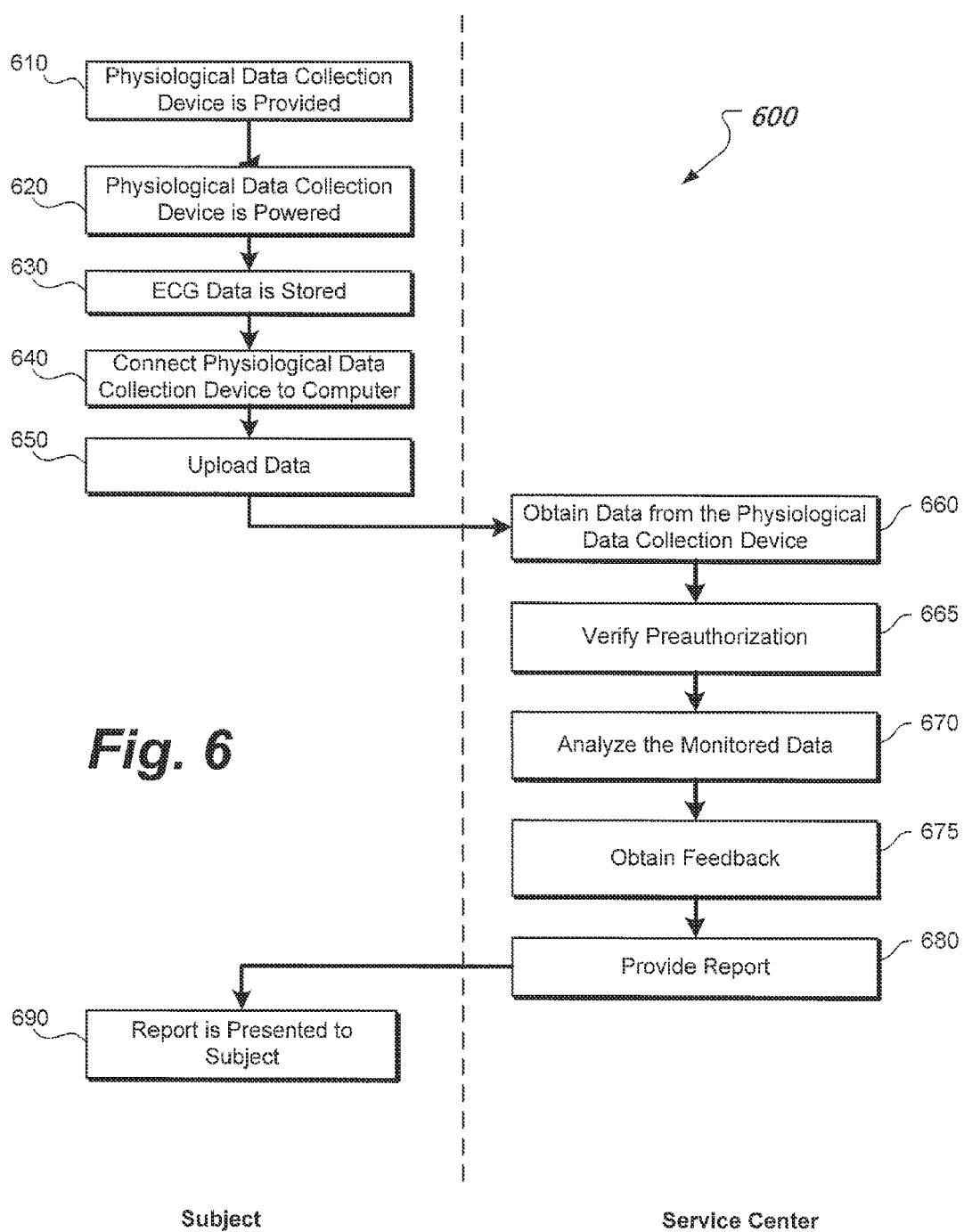
FIG. 6 shows an example process for obtaining physiological data from a subject.

FIG. 6 shows an example process 600 for obtaining physiological data from a subject. At 610, a physiological data collection device is provided to a subject. For example, the subject can purchase the physiological data collection device as part of a self-assessment kit such as a one-time use self-assessment kit that is preauthorized to allow a subject to self-record his or her ECG signal for a predetermined time period and to receive an analysis service from a data processing center. The analysis service can include, for example, analysis of the ECG signal for that predetermined time period. The kit can include all the materials necessary for a subject to self-record his or her cardiac activity for the predetermined time period and to obtain a report from a data processing center—including, for example, a data collection unit, electrode leads, sufficient disposable electrodes for the predetermined time period, and program code for allowing the subject to upload data to the data processing center. The physiological data collection device can also include unused memory just sufficient to store ECG data for the predetermined time period, and a battery with just sufficient power for operating the physiological data collection device for the predetermined time period. The physiological data collection device is also configured to connect to a computer, such as a subject's personal computer.

At 620, the physiological data collection device is powered. For example, the physiological data collection device can be powered by an internal battery when the subject connects the electrode leads to the data collection unit, as discussed in more detail below in connection with FIGS. 10 and 13. Also, the data acquisition from the electrode leads can be automatic upon the electrode leads being connected to the physiological data collection device. At 630, ECG data from the subject is stored in memory in the physiological data collection device. At 640, the subject connects the physiological data collection device to a computer. The subject can connect the physiological data collection device to the computer when the data collection is complete, such as when the memory is full, or when the battery dies. The subject connects the physiological data collection device to the computer using, for example, a USB connector on the physiological data collection device.

The ECG data can be uploaded to the data processing center automatically when the physiological data collection device is connected to the computer. For example, the computer can run a software application that obtains data from the memory, including ECG data, and transfers the ECG data to the data processing center. In some examples, such a software application can be installed on the computer. In some examples, program code can be stored on the memory of the physiological data collection device that auto-runs when the physiological data collection device is connected to the computer. The auto-run program code can prompt the user to download an application from a remote server for uploading the data from the physiological data collection device. In some examples, the auto-run program code can direct the subject to a remote application, such as a website, that directs the subject to upload data from the physiological data collection device without installing an application on the computer.

At 660, data from the physiological data collection device is obtained by the data processing center. At 665, the data processing center verifies, based on the uploaded data, whether the physiological data collection device is pre-authorized for an analysis service. For example, the data processing center can check a unique identifier of the physiological data collection device, such as a serial number, to determine if the physiological data collection device is preauthorized for the analysis service. The data processing center can also check to determine whether an analysis service has already been provided for the physiological data collection device. If the physiological data collection device is not pre-authorized, or if an analysis service has already been provided for the pre-authorized physiological data collection device, the data processing center can indicate as much to the subject and prompt the subject for payment for the analysis service. If authorization is verified and if a data processing service has not been provided for the physiological data collection device, the data processing center, at 670, analyzes the ECG data from the physiological data collection device for arrhythmia events. Predetermined computer algorithms can be used to analyze the ECG data for arrhythmia events.

At 675, the data processing center can obtain feedback from a medical professional, such as a medical technician and/or a doctor. For example, the identified arrhythmic events are provided to a medical professional for further analysis and/or review. The medical professional can determine the accuracy of the identified events and provide feedback to the data processing center. Based on the analysis performed at 670 and based on the feedback 675, a report is provided to the subject at 680. At 690, the report is presented to the subject. The report can be provided to the subject in various ways, such as by mail, by phone, by fax, by email, or by a software application. An application on the subject's computer (such as an application used to upload ECG data to the data processing center), can be configured to obtain the report from the data processing center and to present the report to the subject. In some examples, the application can be a web-based application. The subject can be notified that his or her report is available. And, the subject can log-on to the web-based application, to view the report. The report can also contain a recommendation to the subject to consult his or her personal physician based on the results of the report, such as when the analysis identifies clinically significant arrhythmic events.

Figure 7:
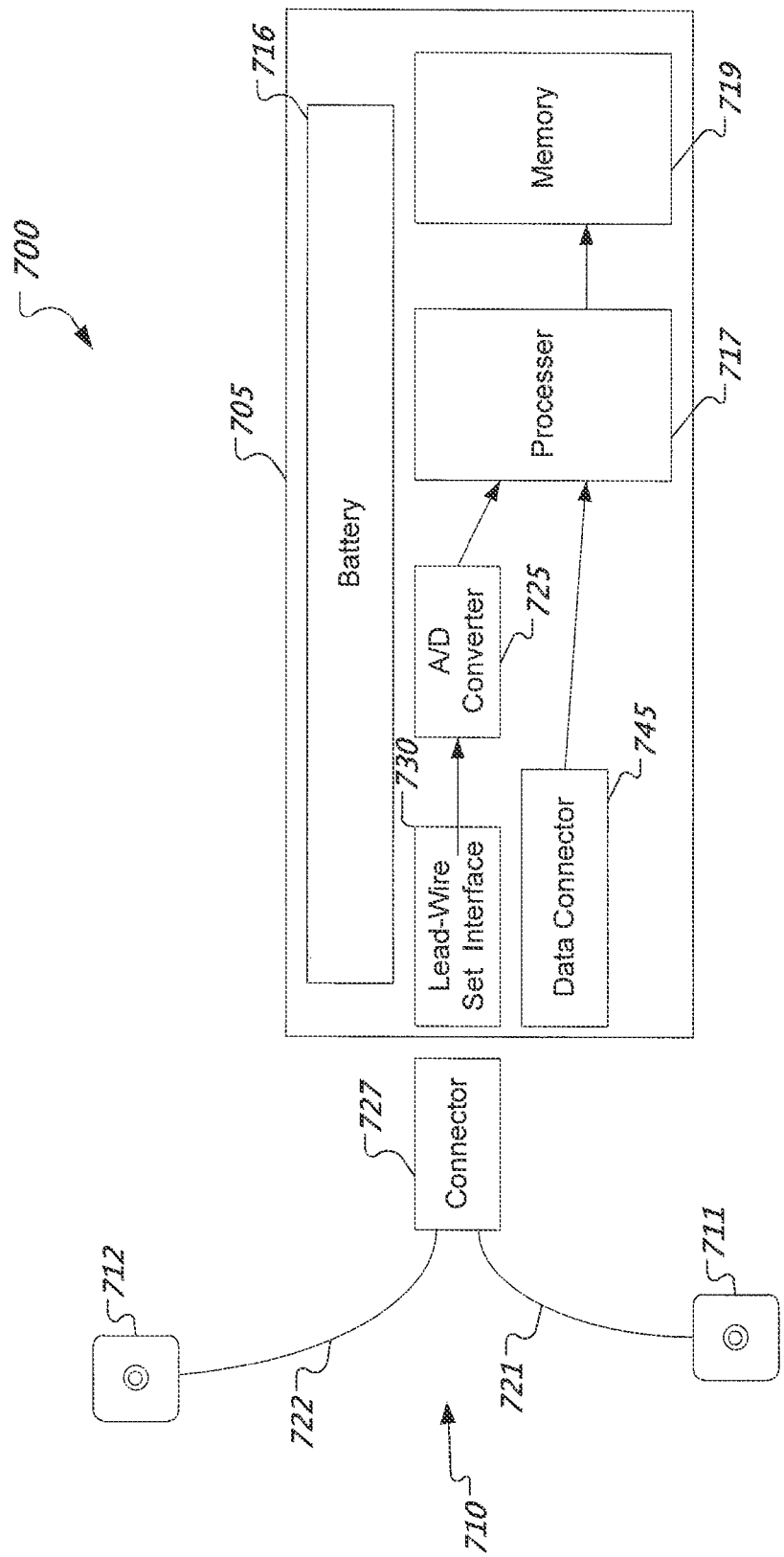
FIG. 7 shows a schematic of an example physiological data collection device.

FIG. 7 shows a schematic of an example physiological data collection device 700. The physiological data collection device 700 has a data collection unit 705 and a lead-wire set 710. The data collection unit 705 includes a battery 716 that powers processor electronics in the data collection unit 705 including a processor 717 such as a multifunction processor, memory 719, and an analog-to-digital ("A/D") converter 725. The battery 716 can be large enough to run the physiological data collection device 700 for a predefined time period. The memory can be non-volatile memory, such as flash memory. The lead-wire set 710 includes electrodes 711 and 712 which are connected to electrode leads 721 and 722. The electrode leads 721 and 722 are connected to a lead-wire set connector 727 which in turn can be physically connected to the data collection unit 705 via a lead-wire set interface 730.

Analog signal data is obtained from the lead-wire set 710 over the lead-wire set interface 730. The analog signal is digitized by the A/D converter 725 and stored by the processor in the memory 719. In order to reduce costs and size, the data collection unit 705 can have just sufficient memory 719 for storing the digitized data from a subject obtained over a predefined time period. In some examples, the data collection unit can have just sufficient memory for the digitized data and for program code necessary for supporting access to a remote data processing center so that the digitized data can be uploaded to the data processing center.

The data collection unit 705 can be plugged into a computer via a data connector 745. The data connector 745 can be a USB data connector, a firewire connector, a serial port connector, or the like. When the data collection unit 705 is plugged into a computer such as via USB, computer power is sensed by the processor 717. The processor 717 can then transfer the digitized data from the memory 719 to the computer for uploading to a remote data processing center.

Figure 8B:
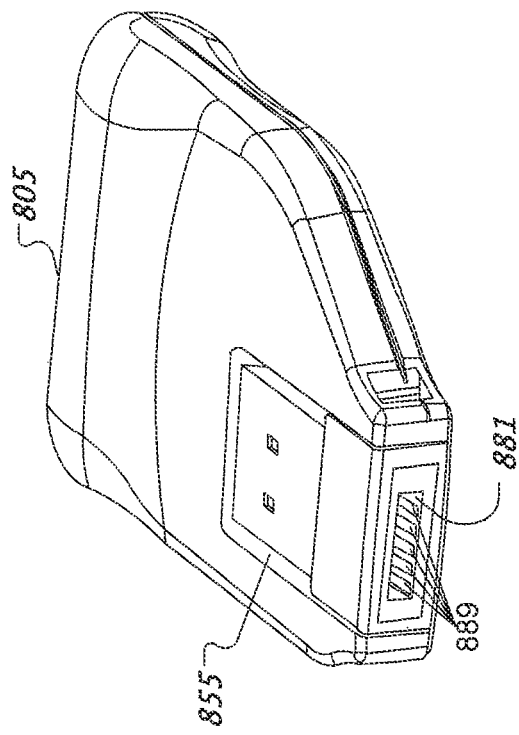
FIGS. 8A and 8B show an example data collection unit.
Figure 8A:
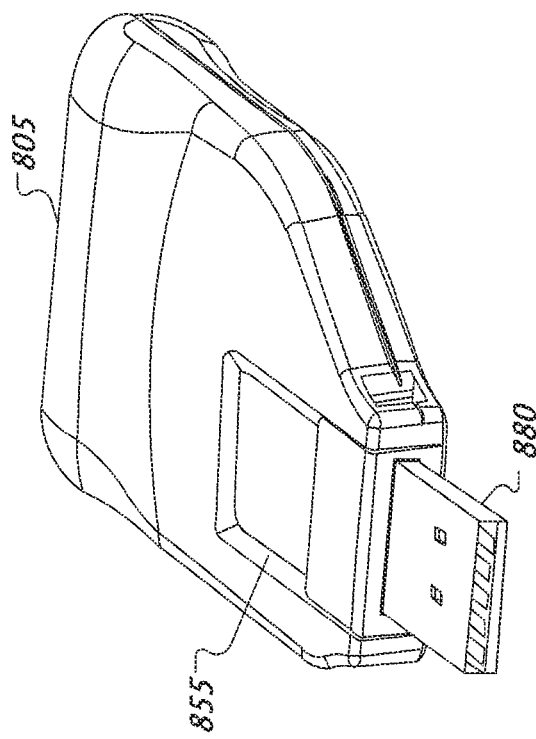

FIGS. 8a and 8b show an example data collection unit 805. The data collection unit 805 prevents a subject from connecting an electrode to the data collection unit 805 at the same time the data collection unit 805 is connected to an external device such as the subject's computer. As shown in FIG. 8a, the data collection unit 805 has a USB connector 880 for connecting to an external computer. Data stored on the data collection unit 805, such as ECG data, can be uploaded to a computer via the USB connector 880.

When the data collection unit 805 is used to obtain ECG data, the USB connector 880 is rotated 180 degrees so that the USB connector 880 is nestled in a recess 855 in the data collection unit 805 as shown in FIG. 8b. When the USB connector 880 is nestled in the recess 855, a female electrode connector receptacle 881 is exposed. The electrode connector receptacle 881 receives an electrode connector on a lead-wire set (not shown). The electrode connector has lead-wire set contacts that make contact with data collection unit contacts 889 in the electrode connector receptacle 881 when the lead-wire set is connected to the data collection unit 805. The lead-wire set contacts make contact with the data collection unit contacts so that ECG data can be obtained from the lead-wire set. When the lead-wire set is connected to the data collection unit 805, the USB connector 880 cannot be connected to a computer or any other external device because the USB connector 880 is nestled in the recess 855.

In some implementations, a USB connector on a data collection unit can be customized to include data collection unit contacts (in addition to the USB contacts) so that a lead-wire set communicates with the data collection unit through the USB connector by making contact with the data collection unit contacts in the USB connector. The USB connector can still be used to connect the data collection unit to a computer because it has standard USB contacts.

Figure 9B:
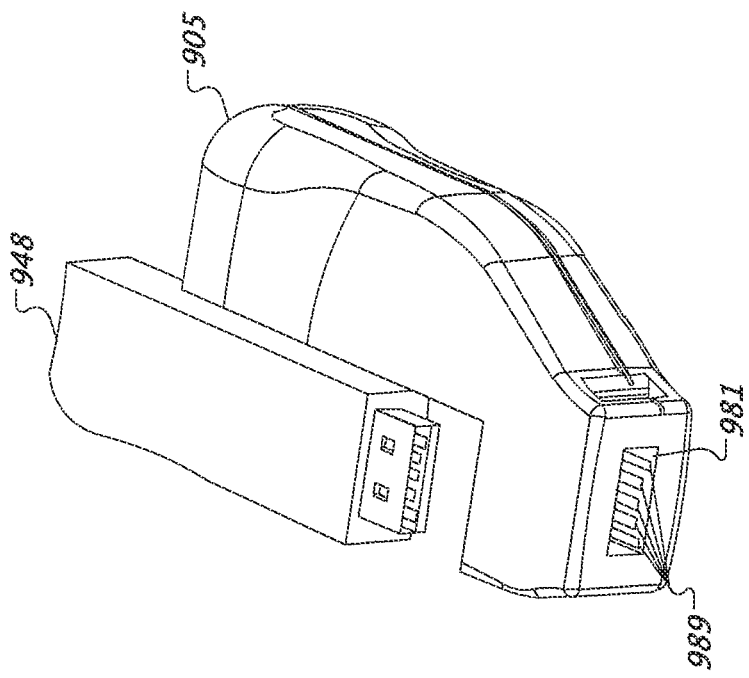
FIGS. 9A and 9B show an example data collection unit.
Figure 9A:
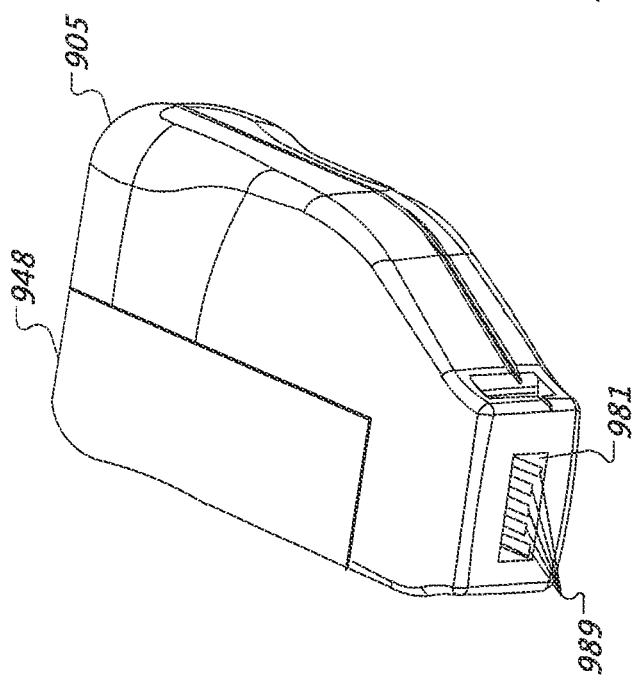

FIGS. 9A and 9B show an example data collection unit 905. The data collection unit 905 has a female electrode connector receptacle 981. Data collection unit contacts 989 are located inside the electrode connector receptacle 981. When a lead-wire set (not shown) is connected to the data collection unit 905, an electrode connector on the lead-wire set is received into the electrode connector receptacle 981 on the data collection unit 905, and lead-wire set contacts on the electrode connector make contact with the data collection unit contacts 989 so that ECG data can be obtained by the data collection unit 905. The ECG data can be digitized and stored on a removable USB device 948 in the data collection unit 905. During data collection from the subject, the USB device 948 is connected to the data collection unit 905 as shown in FIG. 9A. When the ECG data stored on the USB device needs to be uploaded to a computer, the USB device is removed from the data collection unit 905 as shown in FIG. 9B. This configuration physically prevents a subject hooked-up to the data collection unit 905 from being electrically connect to an external device via USB device 948 because the USB device 948 must be removed from the data collection unit 905 in order to be connected to a computer.

Figure 10:
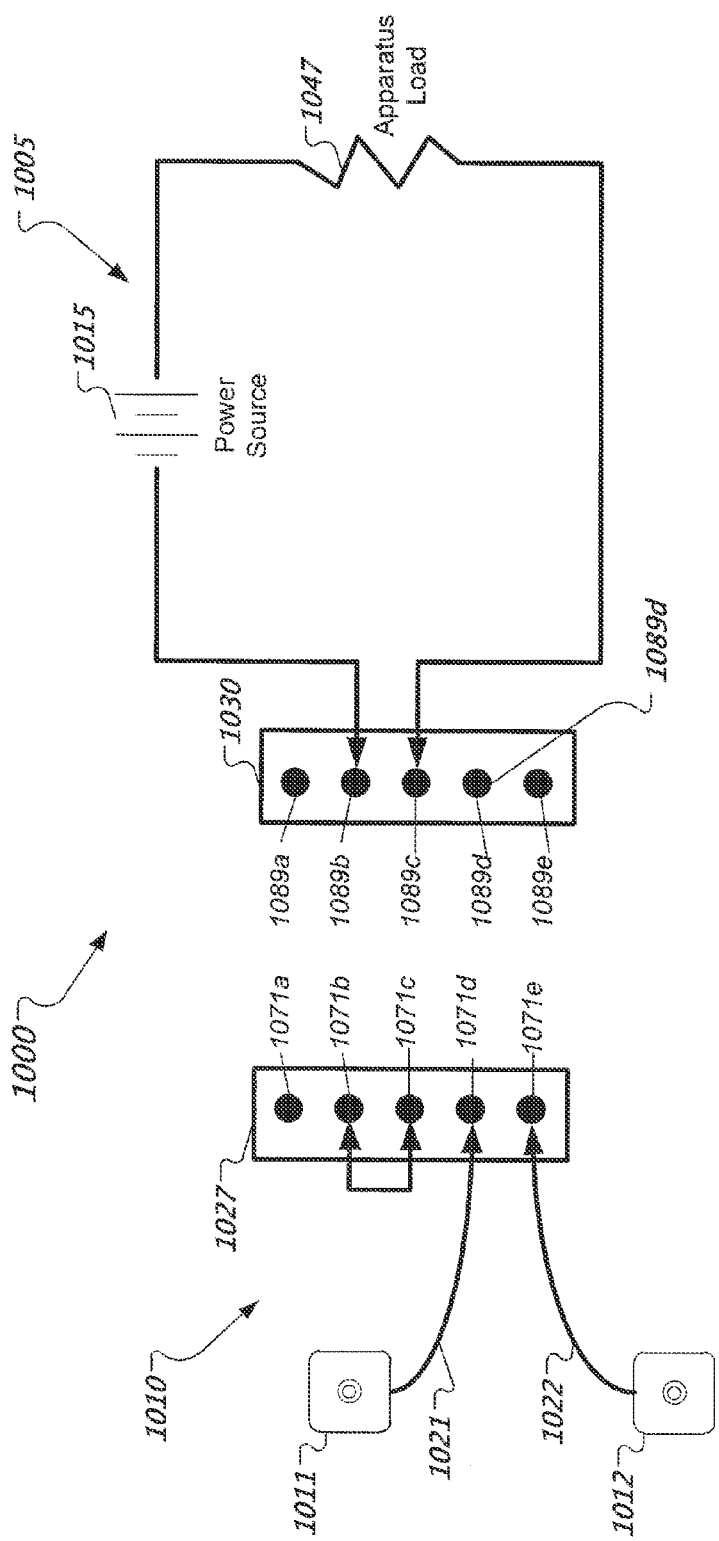
FIG. 10 shows a schematic of an example physiological data collection device.

FIG. 10 shows a schematic of an example physiological data collection device 1000. The physiological data collection device 1000 includes a data collection unit 1005 and a lead-wire set 1010. The data collection unit 1005 includes a power source 1015 that provides power to an apparatus load 1047. The apparatus load can include, for example, processor electronics for obtaining and storing ECG data from the lead-wire set 1010, such as a processor, an A/D converter, non-volatile memory, etc. The data collection unit 1005 also includes a lead-wire set interface 1030. The lead-wire set interface 1030 has five data collection unit contacts—a first data collection unit contact 1089a, a second data collection unit contact 1089b, a third data collection unit contact 1089c, a fourth data collection unit contact 1089d, and a fifth data collection unit contact 1089e.

The lead-wire set 1010 has a lead-wire set connector 1027, a first and second electrode leads 1021 and 1022, and electrodes 1011 and 1012. The lead-wire set connector 1027, when connected to the data collection unit 1005, has five lead-wire set contacts—a first lead-wire set contact 1071a, a second lead-wire set contact 1071b, a third lead-wire set contact 1071c, a fourth lead-wire set contact 1071d, and a fifth lead-wire set contact 1071e—that make contact with the first data collection unit contact 1089a, the second data collection unit contact 1089b, the third data collection unit contact 1089c, the fourth data collection unit contact 1089d, and the fifth data collection unit contact 1089e, respectively.

Two of the lead-wire set contacts are for the electrode leads 1021 and 1022, two are for powering the data collection unit 1005, and one optional the lead wire set contact is for interrupting the processor when the lead-wire set 1010 has been disconnected from the data collection unit 1005. For example, the fourth lead-wire set contact 1071d and the fifth lead-wire set contact 1071e are connected to the first electrode lead 1021 and the second electrode lead 1022. When the fourth lead-wire set contact 1071d and the fifth lead-wire set contact 1071e are in contact with the fourth data collection unit contact 1089d and the fifth data collection unit contact 1089e, an ECG signal can be obtained by the data collection unit 1005 from the electrodes 1011 and 1012.

When the lead-wire set 1010 and the data collection unit 1005 are connected, the second lead-wire set contact 1071b makes contact with the second data collection unit contact 1089b and the third lead-wire set contact 1071c makes contact with the third data collection unit contact 1089c. The second and third lead-wire set contacts 1071b and 1071c close an open circuit in the data collection unit 1005 when the lead-wire set connector is connected to the data collection unit 1005, allowing power to be supplied from the power source 1015 so that the subject's ECG data can be obtained. This allows the data collection unit 1005 to operate as soon as the lead-wire set 1010 is connected. When the lead-wire set 1010 is disconnected, an open circuit is created, terminating power supplied to the apparatus load from the power source 1015. This helps prevent power leakage when the lead-wire set 1010 is disconnected from the data collection unit 1005.

When the lead-wire set 1010 and the data collection unit 1005 are connected, the first lead-wire set contact 1071a makes contact with the first data collection unit contact 1089a. When the lead-wire set 1010 and the data collection unit 1005 are disconnected, contact is broken between the first lead-wire set contact 1071a and the first data collection unit contact 1089a, which in turn sends an interrupt signal to the processor in the data collection unit 1005. The interrupt signal stops the processor from recording data to the non-volatile memory before the capacitance in the opened circuit is lost. The interrupt signal helps prevent the non-volatile memory from becoming corrupted.

In some implementations, other circuitry, such as a real-time clock, can be separately connected to the power source 1015 such that power is supplied to the other circuitry even upon the lead-wire set 1010 being disconnected from the data collection unit 1005. This allows an accurate determination of elapsed time for ECG data obtained by the lead-wire set 1010. The elapsed time from the beginning of recording can be stored with the ECG data obtained from the lead-wire set 1010. In some examples, components not included in the apparatus load can be connected to the power source 1015 separately, but in response to the lead-wire set 1010 being disconnected from the data collection unit 1005, those components can be placed into a standby mode—powered down to a lower operational state to conserve power.

Figure 11:
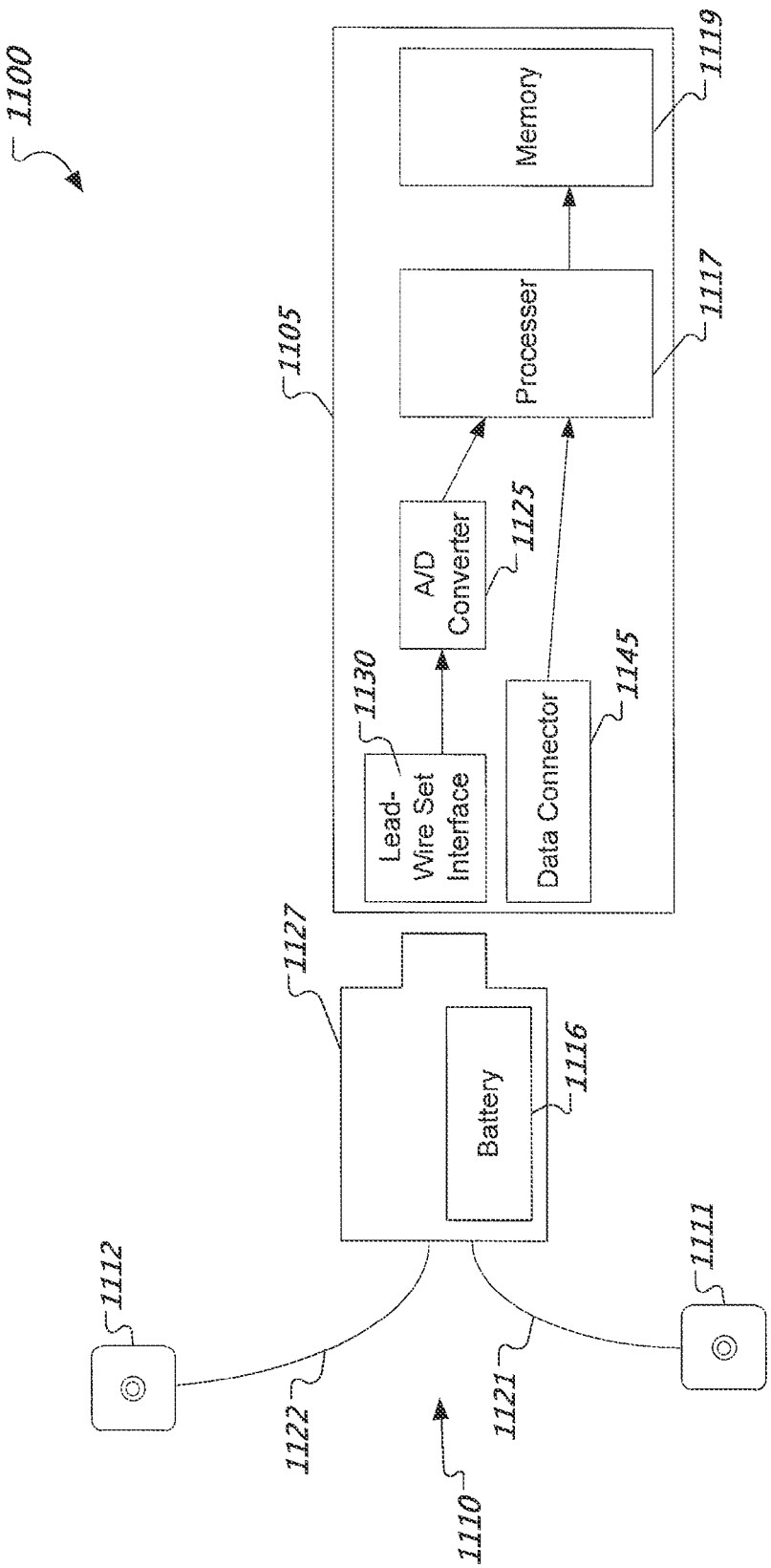
FIG. 11 shows a schematic of an example physiological data collection device.

FIG. 11 shows a schematic of an example physiological data collection device 1100. The physiological data collection device 1100 has a data collection unit 1105 and a lead-wire set 1110. The lead-wire set includes a lead-wire set connector 1127 for connecting the lead-wire set 1110 to the data collection unit 1105. The lead-wire set 1110 includes electrodes 1111 and 1112 which are connected to electrode leads 1121 and 1122. The electrode leads 1121 and 1122 are connected to a lead-wire set connector 1127 which in turn can be physically connected to the data collection unit 1105 via a lead-wire set interface 1130. The lead-wire set also includes a battery 1116 in the lead-wire set connector 1127 that powers the physiological data collection device 1100, including processor electronics in the data collection unit 1105 such as a processor 1117, memory 1119 (e.g. non-volatile memory), and an analog-to-digital ("A/D") converter 1125. The battery 1116 can be large enough to run the physiological data collection device 1100 for a predefined time period. For example, the battery can be large enough to run the physiological data collection device 1100 for a long enough period of time to fill the memory 1119 with data obtained from the lead-wire set 1110. When the battery dies after the predefined time period, it can be disposed of with the disposal of the lead-wire set 1110. As a result, the data collection unit 1105 can be reused for another predefined time period, upon the connection of another lead-wire set with a fresh battery. In some examples, upon the batter dying, the lead-wire set 1110 can be interchanged with another interchangeable lead-wire set with a new battery so that data collection can continue. In some examples, the battery can be removable; when the removable battery dies, the removable battery can be replaced.

Analog signal data is obtained from the lead-wire set 1110 over the lead-wire set interface 1130. The analog signal is digitized by the A/D converter 1125 and stored by the processor 1117 in the memory 1119. In order to reduce costs and size, the data collection unit 1105 can have just sufficient memory 1119 for storing the digitized data from a subject obtained over a predefined time period. In some examples, the data collection unit 1105 can have just sufficient memory for the digitized data and for program code necessary for supporting access to a remote data processing center so that the digitized data can be uploaded to the data processing center.

The data collection unit 1105 can be plugged into a computer via a data connector 1145. The data connector 1145 can be a USB data connector, a firewire connector, a serial port connector, or the like. When the data collection unit 1105 is plugged into a computer such as via USB, computer power is sensed by the processor 1117. The processor 1117 can then transfer the digitized data from the memory 1119 to the computer for uploading to a remote data processing center.

Figure 12:
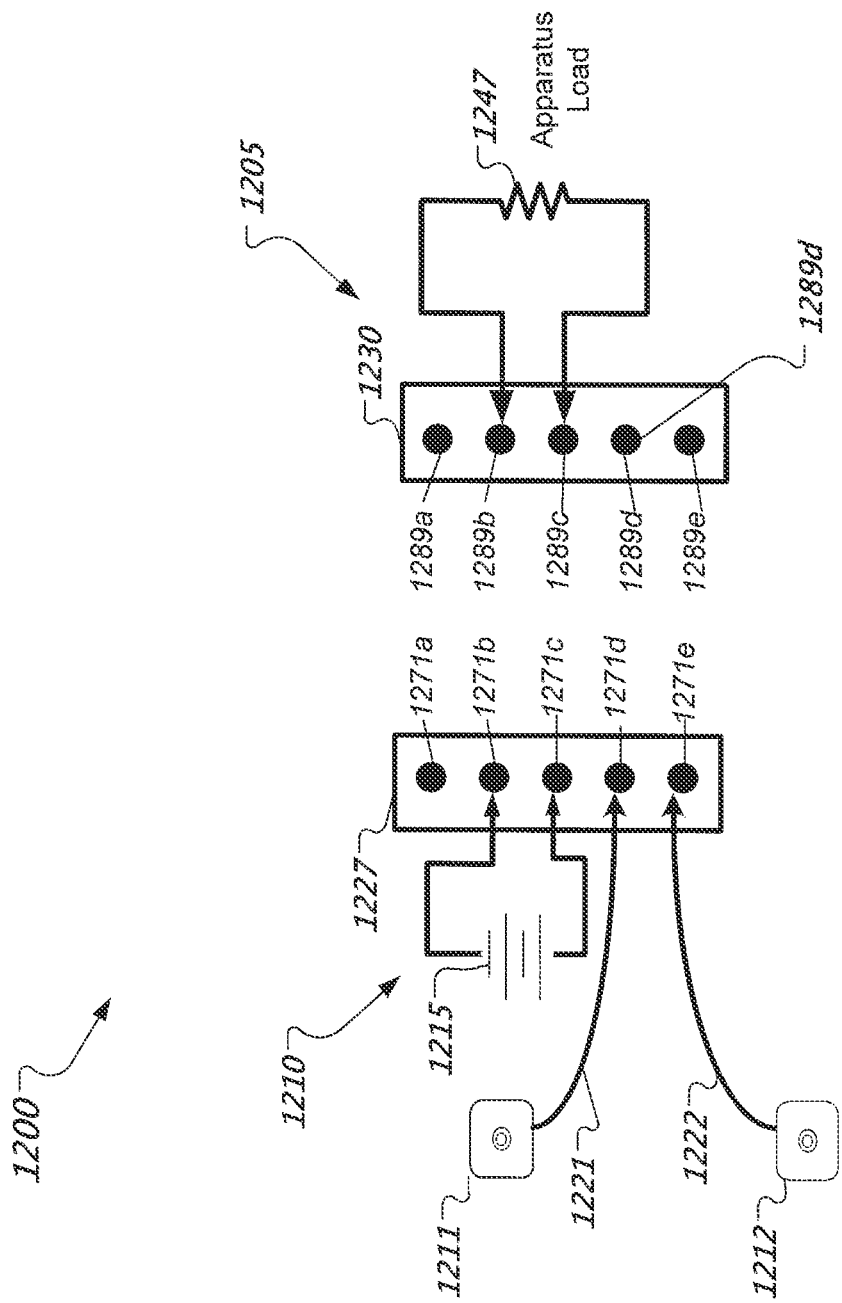
FIG. 12 shows a schematic of an example physiological data collection device.

FIG. 12 shows a schematic of an example physiological data collection device 1200. The physiological data collection device 1200 includes a data collection unit 1205 and lead-wire set 1210. The lead-wire set 1210 includes a power source 1215 that provides power to an apparatus load 1247 when the lead-wire set 1210 is connected to the data collection unit 1205. The apparatus load can include, for example, processor electronics for obtaining and storing ECG data from the lead-wire set 1210, such as a processor, an A/D converter, non-volatile memory, etc. The data collection unit 1205 also includes a lead-wire set interface 1230. The lead-wire set interface 1230 has five data collection unit contacts—a first data collection unit contact 1289a, a second data collection unit contact 1289b, a third data collection unit contact 1289c, a fourth data collection unit contact 1289d, and a fifth data collection unit contact 1289e.

The lead-wire set 1210 has a lead-wire set connector 1227, a first and second electrode leads 1221 and 1222, and electrodes 1211 and 1212. The lead-wire set connector 1227, when connected to the data collection unit 1205, has five lead-wire set contacts—a first lead-wire set contact 1271a, a second lead-wire set contact 1271b, a third lead-wire set contact 1271c, a fourth lead-wire set contact 1271d, and a fifth lead-wire set contact 1271e—that make contact with the first data collection unit contact 1289a, the second data collection unit contact 1289b, the third data collection unit contact 1289c, the fourth data collection unit contact 1289d, and the fifth data collection unit contact 1289e, respectively.

Two of the lead-wire set contacts are for the electrode leads 1221 and 1221, two are for powering the data collection unit 1205, and one optional lead-wire set contacts is for interrupting the processor when the lead-wire set 1210 has been disconnected from the data collection unit 1205. For example, the fourth lead-wire set contact 1271d and the fifth lead-wire set contact 1271e are connected to the first electrode lead 1221 and the second electrode lead 1222. When the fourth lead-wire set contact 1271d and the fifth lead-wire set contact 1271e are in contact with the fourth data collection unit contact 1289d and the fifth data collection unit contact 1289e, an ECG signal can be obtained by the data collection unit 1205 from the electrodes 1211 and 1212.

When the lead-wire set 1210 and the data collection unit 1205 are connected, the second lead-wire set contact 1271b makes contact with the second data collection unit contact 1289b, and the third lead-wire set contact 1271c makes contact with the third data collection unit contact 1289c. The second and third lead-wire set contacts 1271b and 1271c close an open circuit in the data collection unit 1205 when the lead-wire set connector is connected to the data collection unit 1205, allowing power to be supplied from the power source 1215 in the lead-wire set 1215 so that the subject's ECG data can be obtained. This allows the data collection unit 1205 to operate as soon as the lead-wire set 1210 is connected. This also prevents power leakage when the lead-wire set 1210 is disconnected.

When the lead-wire set 1210 and the data collection unit 1205 are connected, the first lead-wire set contact 1271a makes contact with the first data collection unit contact 1289a. When the lead-wire set 1210 and the data collection unit 1205 are disconnected, contact is broken between the first lead-wire set contact 1271a and the first data collection unit contact 1289a, which in turn sends an interrupt signal to the processor in the data collection unit 1205. The interrupt signal stops the processor from recording data to the non-volatile memory before the capacitance in the opened circuit is lost. The interrupt signal helps prevent the non-volatile memory from becoming corrupted.

Figure 13:
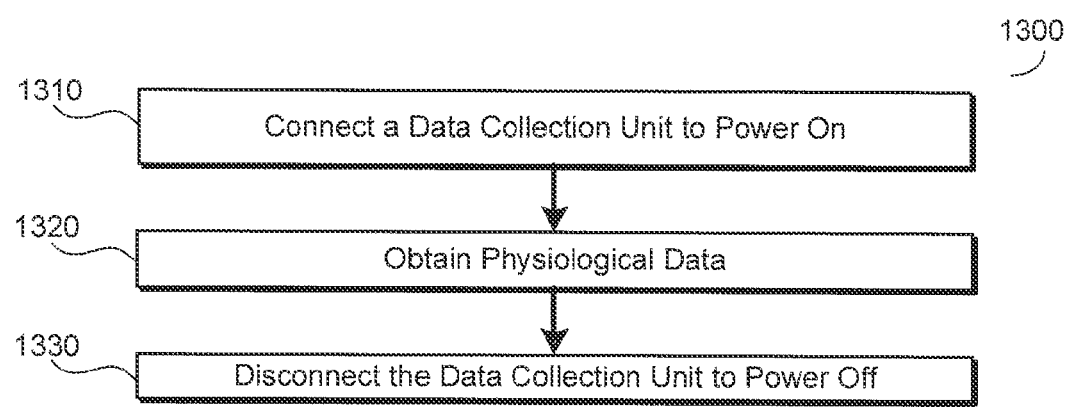
FIG. 13 shows an example process for powering an ECG data collection unit.

FIG. 13 shows an example process 1300 for powering a physiological data collection unit. At 1310, a subject interface is connected to a data collection unit. When the subject interface is connected to the data collection unit, the data collection unit is powered on. The subject interface can power on the data collection unit by closing an open circuit between an apparatus load and a power supply. For example, the power supply can include the power needed to run processing electronics for obtaining ECG data from a subject. The power supply can be located in the data collection unit. In some examples, the power supply can be located in the subject interface. At 1320, physiological data is obtained and stored by the data collection unit. The physiological data can be obtained automatically when the subject interface is connected to the data collection unit. Accordingly, the subject needs only connect the subject interface to the data collection unit to power the data collection unit and to start the data collection unit obtaining and storing data. At 1330, the subject interface is disconnected. When the subject interface is disconnected, the data collection unit powers off. Disconnecting the subject interface can power off the data collection unit by creating an open circuit between the apparatus load and the power supply. Also, the process 1300 can optionally send an interrupt signal to a processor in the data collection unit when the subject interface is disconnected to interrupt storing data to memory in order to prevent the memory from being corrupted. Also, disconnecting the data collection unit stops the obtaining and recording of data from the subject interface.

The disclosed systems, techniques, and all of the functional operations described and illustrated in this specification can be implemented in digital electronic circuitry, or in computer hardware, firmware, software, or in combinations of the forgoing. For example, one or more computers and/or circuitry can be operable to or configured and arranged to perform the functions and techniques disclosed herein. Apparatuses and/or systems can be implemented using a software product (e.g., a computer program code) tangibly embodied in a machine-readable storage device for execution by a programmable processor, and processing operations can be performed by a programmable processor executing a program of instructions to perform functions by operating on input data and generating output. Further, the system can be implemented advantageously in one or more software programs that are executable on a programmable system. This programmable system can include the following: 1) at least one programmable processor coupled to receive data and instructions from, and to transmit data and instructions to, a data storage system; 2) at least one input device; and 3) at least one output device. Moreover, each software program can be implemented in a high-level procedural or object-oriented programming language, or in assembly or machine language if desired; and in any case, the language can be a compiled or an interpreted language.

Also, suitable processors include, by way of example, both general and special purpose microprocessors. Generally, a processor will receive instructions and data from a read-only memory, a random access memory, and/or a machine-readable signal (e.g., a digital signal received through a network connection). The essential elements of a computer are a processor for performing instructions and one or more memory devices for storing instructions and data. Generally, a computer will include one or more mass storage devices for storing data files. Such devices can include magnetic disks, such as internal hard disks and removable disks, magneto-optical disks, and optical disks. Storage devices suitable for tangibly embodying software program instructions and data include all forms of non-volatile memory, including, by way of example, the following: 1) semiconductor memory devices, such as EPROM (electrically programmable read-only memory); EEPROM (electrically erasable programmable read-only memory) and flash memory devices; 2) magnetic disks such as internal hard disks and removable disks; 3) magneto-optical disks; and 4) CD-ROM disks. Any of the foregoing can be supplemented by, or incorporated in, ASICs (application-specific integrated circuits).

The disclosed systems and techniques, described and illustrated in this specification can be implemented using a communications network such as a wired or wireless network. Examples of communication networks include, e.g., a local area network ("LAN"), a wide area network ("WAN"), the Internet or any combinations of such.

To provide for interaction with a user (such as the health care provider), systems can be implemented on a computer system having a display device such as a monitor or LCD (liquid crystal display) screen for displaying information to the user and a keyboard and a pointing device such as a mouse or a trackball by which the user can provide input to the computer system. The computer system can be programmed to provide a graphical user interface through which computer programs interact with users.

A number of embodiments have been described. Nevertheless, it will be understood that various modifications may be made without departing from the spirit and scope of the invention. Accordingly, other embodiments are within the scope of the following claims.

What is claimed is:

1. An ECG kit comprising:
   a wearable ECG data collection unit comprising:
   a non-volatile memory;
   a processor electrically connected to the non-volatile memory and configured to store ECG data in the non-volatile memory and upload ECG data from the non-volatile memory; and
   a male data connector electrically connected to the processor, wherein the male data connector is configured to connect, physically and electrically, to both (i) a wearable ECG subject interface and (ii) a computer data port.

2. The ECG kit of claim 1, wherein the male data connector is a USB connector.

3. The ECG kit of claim 1, wherein the male data connector comprises data collection unit contacts.

4. The ECG kit of claim 3, wherein the male data connector is configured such that the data collection unit contacts electrically connect to contacts of the ECG subject interface when the male data connector is connected to the ECG subject interface.

5. The ECG kit of claim 4, wherein the wearable ECG data collection unit further comprises a power source.

6. The ECG kit of claim 5, wherein the ECG data collection unit is configured to stop providing power from the power source when the ECG subject interface is disconnected from the data collection unit contacts.

7. The ECG kit of claim 6, wherein the ECG data collection unit is further configured to automatically obtain data from the ECG subject interface upon the ECG subject interface being connected to the ECG data collection unit.

8. An ECG kit comprising:
a wearable subject interface; and
a wearable ECG data collection unit comprising:
a non-volatile memory;
a processor electrically connected to the non-volatile memory and configured to store ECG data in the non-volatile memory and upload ECG data from the non-volatile memory; and
a male data connector electrically connected to the processor, wherein the data connector is configured to connect, physically and electrically, to both (1) the wearable subject interface and (2) a computer data port.

9. The ECG kit of claim 8, wherein the male data connector is a USB connector.

10. The ECG kit of claim 8, wherein the male data connector comprises data collection unit contacts.

11. The ECG kit of claim 10, wherein the subject interface includes lead wire set contacts.

12. The ECG kit of claim 11, wherein the data connector is configured such that the lead wire set contacts on the subject interface are electrically connected to the male data connector when the male data connector is connected to the subject interface.

13. The ECG kit of claim 12, wherein the ECG data collection unit further comprises a power source.

14. The ECG kit of claim 13, wherein the ECG data collection unit is configured to stop providing power from the power source when the subject interface is disconnected from the data collection unit contacts.

15. The ECG kit of claim 8, wherein the ECG data collection unit further comprises a first data collection unit contact and a second data collection unit contact, and wherein the subject interface comprises a first subject interface contact and a second subject interface contact that:
when not connected to the first data collection unit contact and the second data collection unit contact, respectively, are configured to create an open circuit, and
when connected to the first data collection unit contact and the second data collection unit contact, respectively, are configured to create a closed circuit.

16. The ECG kit of claim 15, wherein the first data collection unit contact is in series with the second data collection unit contact, and wherein the subject interface, when connected to the data collection unit contacts, is configured to bring the first data collection unit contact into electrical connection with the second data collection unit contact.

17. The ECG kit of claim 8, wherein the subject interface comprises a pair of electrodes.

18. The ECG kit of claim 17, wherein the subject interface contacts comprise a third subject interface contact and a fourth subject interface contact for bringing the pair of electrodes into electrical communication with the processor.

19. The ECG kit of claim 8, wherein the ECG data collection unit is further configured to automatically obtain data from the subject interface upon the subject interface being connected to the ECG data collection unit.

20. The ECG kit of claim 8, wherein the ECG data collection unit is configured to automatically stop obtaining data from the subject interface upon the subject interface being disconnected from the ECG data collection unit.

* * * * *